(12) United States Patent
Tosetti et al.

(10) Patent No.: US 8,926,322 B2
(45) Date of Patent: Jan. 6, 2015

(54) CENTRIFUGAL DEFLECTION DEVICE FOR A SURGICAL OR DENTAL HANDPIECE FOR REMOVING FOREIGN MATTER

(75) Inventors: Marc Tosetti, Cortaillod (CH); Nicola Mikic, La Chaux-de-Fonds (CH); Luc Maitre, Epauvillers (CH)

(73) Assignee: Bien-Air Holding S.A., Bienne (CH)

( * ) Notice: Subject to any disclaimer, the term of this patent is extended or adjusted under 35 U.S.C. 154(b) by 460 days.

(21) Appl. No.: 12/987,271

(22) Filed: Jan. 10, 2011

(65) Prior Publication Data

US 2011/0171594 A1 Jul. 14, 2011

(30) Foreign Application Priority Data

Jan. 14, 2010 (EP) .................................... 10150741

(51) Int. Cl.
| | | |
|---|---|---|
| *A61C 1/16* | (2006.01) | |
| *A61C 1/08* | (2006.01) | |
| *A61C 1/05* | (2006.01) | |
| *A61C 1/10* | (2006.01) | |

(52) U.S. Cl.
CPC . *A61C 1/08* (2013.01); *A61C 1/057* (2013.01); *A61C 1/10* (2013.01)
USPC ......................................................... 433/116

(58) Field of Classification Search
CPC .......... A61C 1/05; A61C 1/052; A61C 1/057; A61C 1/08; A61C 1/10–1/141; A61C 1/144; A61C 1/181; A61C 1/185; A61C 17/005; F16J 15/52; F16J 15/525; B23B 31/001; B23B 31/202; B23B 2231/2021
USPC ......... 433/103, 114, 115, 116, 127, 130, 132; 74/18; 279/43.9, 46.9, 157
See application file for complete search history.

(56) References Cited

U.S. PATENT DOCUMENTS

| | | | |
|---|---|---|---|
| 3,426,429 A | | 2/1969 | Hoffmeister et al. |
| 4,369,034 A | * | 1/1983 | Garnier et al. ................ 433/115 |
| 5,676,542 A | | 10/1997 | Lingenhole et al. |
| 5,692,903 A | * | 12/1997 | Nakanishi ..................... 433/116 |
| 5,823,774 A | | 10/1998 | Abbott et al. |
| 2002/0110781 A1 | * | 8/2002 | Nakanishi ..................... 433/132 |

FOREIGN PATENT DOCUMENTS

| | | |
|---|---|---|
| EP | 0 471 916 B1 | 1/1991 |
| EP | 1 025 809 A2 | 8/2000 |

OTHER PUBLICATIONS

European Search Report for corresponding European Patent Application No. 10150741 dated Jun. 15, 2010.

* cited by examiner

*Primary Examiner* — Cris L Rodriguez
*Assistant Examiner* — Justin O'Donnell
(74) *Attorney, Agent, or Firm* — Sughrue Mion, PLLC (57) ABSTRACT

Centrifugal deflection device intended to be fitted to a surgical or dental handpiece to prevent the penetration of foreign matter that results from an operation, the centrifugal deflection device including a ring coupled in rotation either directly or via a tool shank to a drive shaft of the handpiece. This device is characterized in that the ring is covered by a sleeve secured to the front end of the body of the handpiece and which, with the ring, delimits an ejection chamber. The ejection chamber includes an inlet that communicates with a rear area of the handpiece and an outlet that communicates with the external environment, the ring having a first diameter at the outlet of the ejection chamber and a second diameter at the inlet of the ejection chamber, the first diameter of the ring being larger than the second diameter of the ring.

15 Claims, 6 Drawing Sheets

CENTRIFUGAL DEFLECTION DEVICE FOR A SURGICAL OR DENTAL HANDPIECE FOR REMOVING FOREIGN MATTER

BACKGROUND

1. Field

The present invention concerns a centrifugal deflection device intended to be fitted to a surgical or dental handpiece for removing the foreign matter that results from an operation. More specifically, this invention concerns a device of this type that includes a ring preventing foreign matter that results from an operation from penetrating the handpiece to which the ring is fitted.

2. Related Art

An operation such as the removal of a wisdom tooth inevitably produces debris such as bone or tooth fragments, blood or secretions of saliva. It is imperative that this debris is removed to leave the operating field clean so that the practitioner can clearly see the work he is carrying out. The debris must also be prevented from penetrating the handpiece because it is liable both to damage and to contaminate the instrument.

A device for preventing foreign matter from penetrating the rear zone of a dental handpiece is known from EP Patent Application No. 0 471 916 A1. This handpiece includes a body, a gripper section and a nose section. The nose section includes a main member and a cap, detachably mounted for example by screws, to the main member of the nose section. The cap is provided with four radial, equiangularly spaced evacuation apertures. A sleeve for receiving and securing a dental tool in cooperation with a drive shaft is radially mounted on the foremost end of the drive shaft. An end cap forming an additional rotating member is screwed onto the outer periphery of the sleeve. The end cap has an inner flange in contact with the dental tool and an outer flange extending radially outwardly. An annular chamber communicating at one end with an opening for inserting a dental tool and at the other end with the front face of a bearing located in the rear area of the instrument is delimited between the outer periphery of the end cap and the nose cap.

The device for preventing foreign matter from penetrating the handpiece briefly described above operates as follows. When the drive shaft is rotating, the sleeve and the end cap rotate together, which induces a flow of air around these elements. Given that the radius of rotation of the end cap is larger than that of the sleeve, the circumferential velocity of the end cap is higher than that of the sleeve. Above all, the radius of rotation of the outer flange is the largest and hence the air flow velocity around the outer periphery of the outer flange is the highest so that the air pressure around the outer flange is lower in proximity to the foremost part of the handpiece. A pressure gradient is thus created, which decreases progressively from the dental tool insertion opening towards the inside of the handpiece. During the operation, foreign matter such as debris from the tooth being treated penetrates the handpiece through the dental tool insertion opening and is sucked up by the pressure gradient effect into the inside of the handpiece. This debris moves around in the annular chamber in which the pressure is lower until it reaches the outer flange where the pressure is the lowest. The debris is then expelled towards the exterior through the evacuation apertures by the centrifugal force effect of the end cap. Thus, foreign matter is prevented from penetrating the rear area of the instrument.

It is clear that, in the case of the device disclosed in the aforementioned EP Patent Application No. 0 471 916 A1, the air flow pressure decreases the more the air flow penetrates the handpiece. It therefore seems, from the foregoing, that the front face of the bearing located in the rear area of the handpiece is suitably protected by the outer flange of the end cap, which deflects foreign matter towards the evacuation apertures and forms an obstacle preventing the foreign matter from moving forward towards the front face of the bearing. However, the device described above does not totally prevent debris from penetrating the handpiece. Indeed, debris penetrates the handpiece through the dental tool insertion opening and moves around inside the annular chamber delimited between the nose cap and the outer periphery of the end cap. The debris thus inevitably dirties these elements and may even reach the drive shaft and alter the working of the handpiece. Consequently, between two successive patients, the entire nose section has to be dismantled from the handpiece, namely the nose cap, the end cap and the sleeve so that these elements can be cleaned and the handpiece completely sterilised, which is difficult and time consuming.

BRIEF SUMMARY

It is thus an object of this invention to overcome the aforementioned drawbacks in addition to others by providing a centrifugal deflection device for a surgical or dental handpiece that really stops any foreign matter from entering the inside of the handpiece.

This invention therefore concerns a centrifugal deflection device intended to be fitted to a surgical or dental handpiece for preventing any foreign matter that results from an operation from penetrating said handpiece, this centrifugal deflection device including a ring coupled in rotation either directly, or via a tool shank, to a drive shaft of the handpiece, this device being characterized in that the ring is covered by a sleeve which is fixed to the front end of the handpiece body and which delimits an ejection chamber with the ring, this ejection chamber including an inlet that communicates with a rear area of the handpiece and an outlet that communicates with the external environment, the ring having a first diameter at the ejection chamber outlet and a second diameter at the ejection chamber inlet, the first ring diameter being greater than the second ring diameter.

Owing to these features, this invention provides a centrifugal deflection device including a ring which, while being driven either directly by the handpiece drive shaft, or via the tool shank, induces an air flow into an ejection chamber located between the ring and a sleeve fixedly mounted on the front end of the handpiece body. Moreover, given that the first ring diameter at the ejection chamber outlet is larger than the second ring diameter at the ejection chamber inlet, the circumferential speed of the ring at the ejection chamber outlet is higher than the circumferential speed of the ring at the ejection chamber inlet. Consequently, the air flow velocity around the outer periphery of the part of the ring with the largest diameter is the highest so that the air pressure around the part of the ring with the largest diameter is lower than the pressure at the part of the ring with the smallest diameter. A pressure gradient is therefore created in the ejection chamber which decreases from the inside of the handpiece towards the outside thereof. By this pressure gradient effect, an air flow is expelled from the handpiece and prevents debris from the operating field penetrating the instrument. Unlike the prior art where debris is sucked up inside the handpiece, this invention teaches preventing the debris penetrating the interior of the handpiece by using an air flow which is discharged from the handpiece. The risk of the debris penetrating the handpiece and jamming the mechanism thereof is avoided. Moreover, the maintenance and sterilising of a handpiece fitted with a ring according to the invention are greatly facilitated.

If the ring and the sleeve are detachable, this invention advantageously enables existing handpieces to achieve a higher standard by giving them an additional function without requiring any alteration thereto.

According to a complementary feature of the invention, the profile of the ejection chamber and the axis of symmetry of the tool form a non zero angle that extends on either side of a range centred around a value of 90°, which corresponds to a position in which the profile of the ejection chamber is perpendicular to the axis of symmetry of the tool.

According to another feature of the invention, the opposite walls of the rotating ring and the fixed sleeve extend substantially parallel to each other.

BRIEF DESCRIPTION OF THE DRAWINGS

Other features and advantages of the present invention will appear more clearly from the following detailed description of one embodiment of the centrifugal deflection device according to the invention, this example being given solely by way of non-limiting illustration with reference to the annexed drawing, in which.

DETAILED DESCRIPTION OF EXEMPLARY EMBODIMENTS

This invention proceeds from the general inventive idea that consists in fitting a surgical or dental handpiece with a centrifugal deflection device including a ring whose function is to prevent any foreign matter from penetrating the handpiece. Thus, the ring which rotates at the same time as the handpiece drive shaft creates a pressure gradient inside the handpiece that decreases from the interior towards the exterior of said handpiece. This pressure gradient induces an air flow which is discharged through the front of the handpiece. This air flow drives out the foreign matter (tooth or bone debris, blood secretions or saliva) from the work area. By repulsing the foreign matter and consequently preventing it from penetrating the handpiece, the risk of damaging the instrument is avoided and cleaning and sterilising operations are made considerably easier.

In the following description, the spatial orientation of the various elements of the centrifugal deflection device according to the invention will be identified with respect to the front and rear of the handpiece, where the front end of the handpiece is located on the side of the tool shank insertion opening and the rear end of the handpiece is located on the side via which the user holds the handpiece in his hand.

Figure 1:
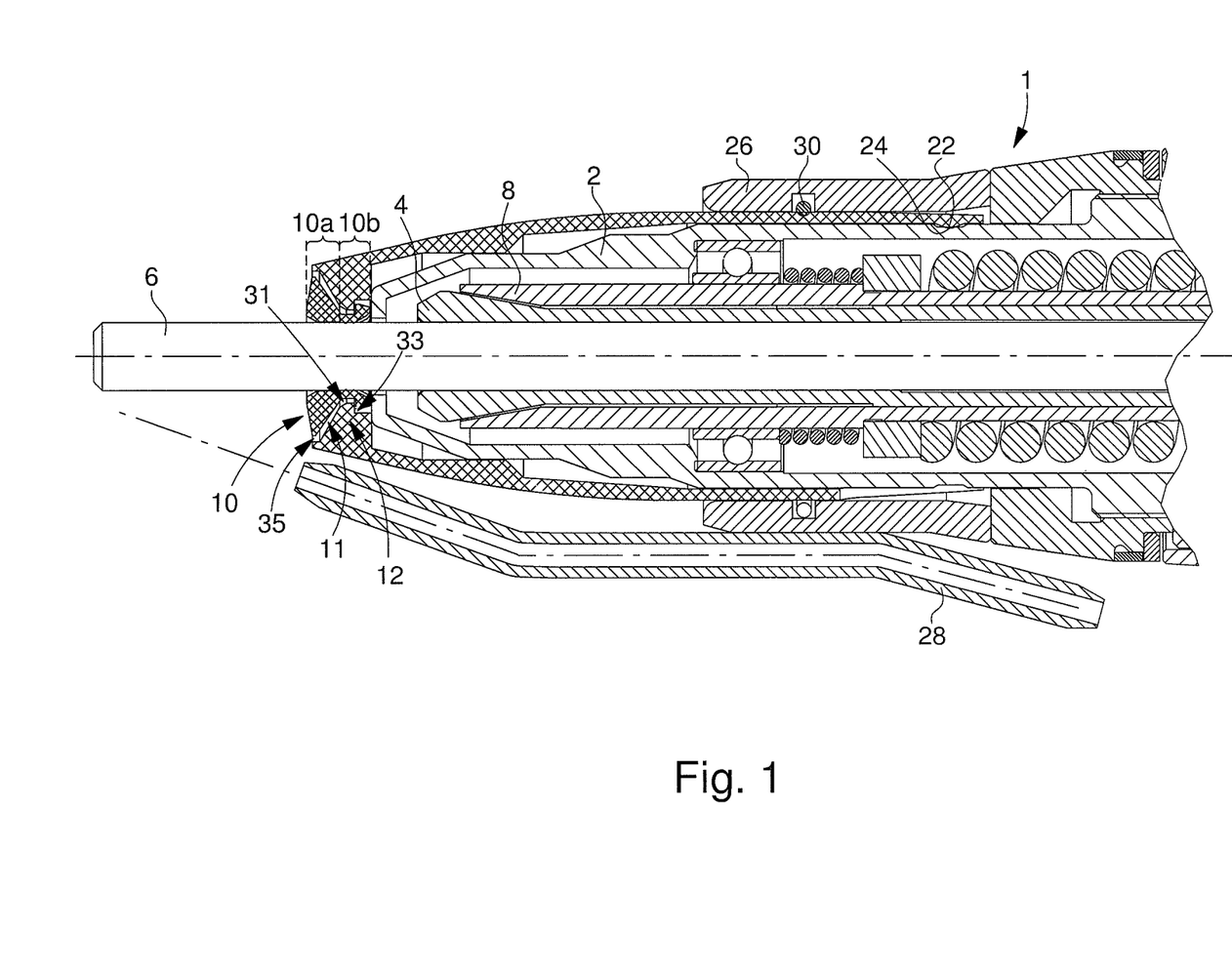
FIG. 1 is a longitudinal cross-section of a handpiece fitted with the centrifugal deflection device according to the invention.

FIG. 1 is a partial longitudinal cross-section of a handpiece fitted with the foreign matter deflection device according to the invention. Designated as a whole by the general reference numeral 1, this handpiece notably includes a clamp 4 for rigidly coupling a tool shank 6 to a drive shaft 8 of handpiece 1, contained within a body 2.

The deflection device according to the invention includes a ring 10, which is a revolution part and which includes from the front to the back end of handpiece 1 a front active section 10a, covered by a sleeve 12 with which the front active section 10a delimits an ejection chamber 11 of substantially annular shape. Ring 10 further includes a rear section 10b useful both for the axial locking and friction assembly thereof on tool shank 6. Ring 10 thus rotates at the same time and at the same speed as tool shank 6.

Figure 2:
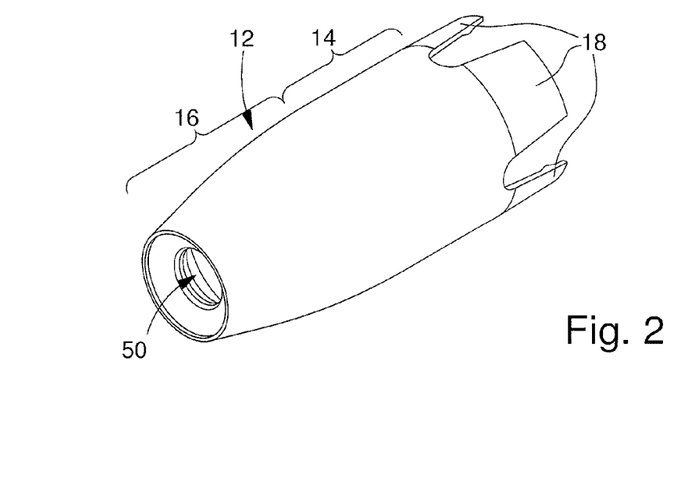
FIG. 2 is a perspective view of the sleeve which, with the centrifugal deflection ring, delimits an ejection chamber of substantially annular shape inside which a pressure gradient is created.
Figure 3:
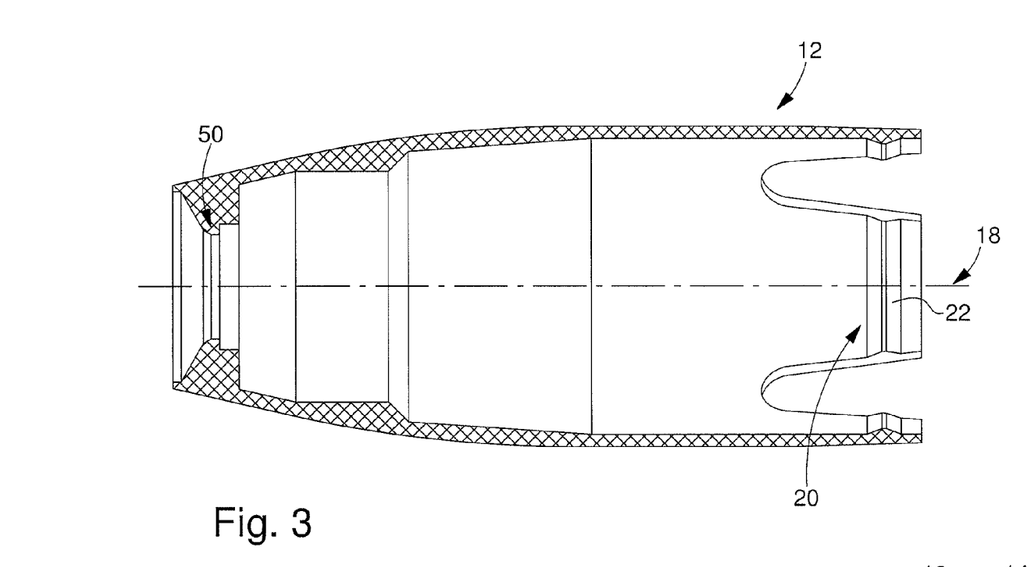
FIG. 3 is a longitudinal cross-section of the sleeve of FIG. 2.

As will be seen in detail below, ring 10 can rotate freely relative to sleeve 12 but is axially locked by said sleeve 12. Sleeve 12 is rib-shaped with a cylindrical portion 14 extended towards the front end of handpiece 1 via a substantially conical portion 16 (see FIG. 2). Sleeve 12 is locked axially on body 2 of handpiece 1. Thus, sleeve 12 is extended towards the rear end of handpiece 1 by a plurality of arms 18 (four in the example shown), which extend tangentially to body 2 of handpiece 1 and which have, on the face 20 thereof facing body 2 of handpiece 1, beads 22 which engage in an opposite radial groove 24 provided on the outer face of body 2 of handpiece 1 (see FIGS. 1 and 3).

As can be seen upon examining FIG. 1, sleeve 12 is arranged concentrically between body 2 of handpiece 1 and an outer ring 26, which carries a stainless steel conduit 28. This conduit 28 is intended to be connected, via a flexible tube (not shown), to a supply of physiological saline solution used for lubricating and cooling the working area of the tool. Outer ring 26 is locked on sleeve 12 by means of a spring wire 30.

Ejection chamber 11 (see FIG. 5) has an inlet 31 that communicates with a rear area 33 of handpiece 1 and an outlet 35 that communicates with the external environment. At the outlet 35 of ejection chamber 11, the front active section 10a of ring 10 has a first diameter referenced D1 and it is connected to the rear section 10b, which has a diameter D2, by an intermediate section, whose largest diameter, is referenced D3. More specifically, ring 10 includes a flange 32 centred on tool shank 6 and whose diameter decreases in the direction of the rear end of handpiece 1. This flange 32 has a conical shape with a truncated portion 34, whose second diameter D4, which is smaller than first diameter D1, is located at the inlet 31 of ejection chamber 11 and is equal to the diameter D3 of the intermediate section. Further, on the front end side of handpiece 1, flange 32 has an annular surface 36.

Figure 5:
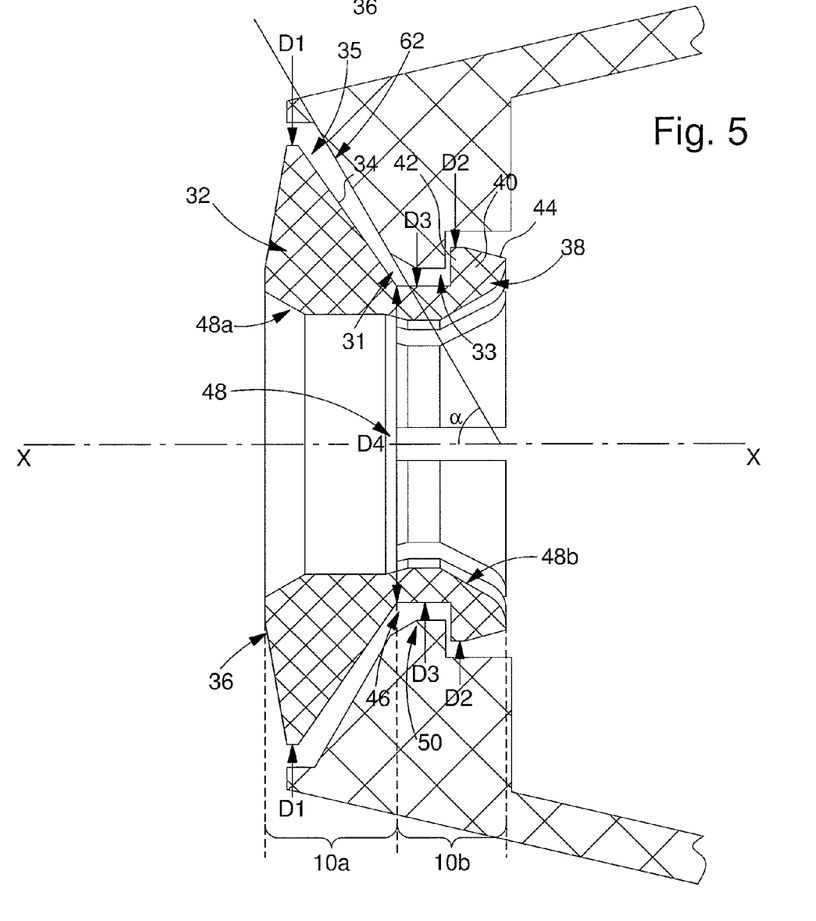
FIG. 5 is a larger scale view of the front part of the handpiece illustrated in FIG. 1.

The opposite walls of rotating ring 10 and fixed sleeve 12 extend substantially parallel to each other at a short distance relative to the difference between first diameter D1 and second diameter D4 of conical flange 32, such that ejection chamber 11 has a substantially constant width. It will also be noted that the active section 10a of flange 32 extends through to the front end of fixed sleeve 12.

Figure 4:
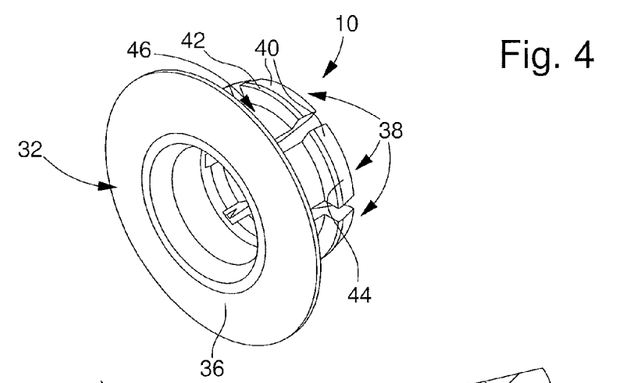
FIG. 4 is a perspective view of the centrifugal deflection ring.

According to the invention, flange 32 is extended in the direction of the rear end of handpiece 1 by a plurality of flexible arms 38 (six in this case), which extend tangentially around tool shank 6 and which end at the free end thereof in a shoulder 40 (see FIG. 4). One of the roles of these flexible arms 38 is to allow ring 10 to be friction fitted onto the tool shank 6. Indeed, the inner diameter of ring 10 is smaller than the external diameter of tool shank 6. By deforming elastically, arms 38 thus enable ring 10 to be engaged on tool shank 6.

For the assembly of ring 10 on tool shank 6, said ring delimits a through hole 48 that emerges, on the front and rear end sides of handpiece 1, on two truncated openings 48a and 48b whose diameters increase towards the ends of handpiece 1.

The largest diameter D1 of flange 32 is larger than the largest diameter D2 of shoulders 40. These shoulders 40 also have, from the front to the back of handpiece 1, a cylindrical section 42 extended by a truncated portion 44, whose diameter decreases towards the rear end of handpiece 1.

Shoulders 40, with flange 32, delimit a circular groove 46 whose diameter D3 is smaller than the smallest diameter of shoulders 40. In fact, the second role of flexible arms 38 is to allow ring 10 to be locked axially on sleeve 12. For this purpose, flexible arms 38 cooperate with means for locking ring 10 axially, which, in one embodiment of the invention, takes the form of a circular inner shoulder 50 provided in sleeve 12 on the front end side of handpiece 1. More specifically, ring 10 is inserted into sleeve 12 on the side of the cone-shaped portion 16 thereof. When arms 38 abut, via their shoulders 40, against circular inner shoulder 50, they deform elastically by moving apart from each other to allow said circular inner shoulder 50 to pass. This movement of deformation is made easier by the presence of truncated portion 44 whose diameter decreases towards the rear end of handpiece 1 and over which circular inner shoulder 50 slides. When circular inner shoulder 50 of sleeve 12 has passed shoulders 40 of arms 38, the latter return to their idle position and circular inner shoulder 50 snaps into circular groove 46. Ring 10 is thus locked axially relative to sleeve 12 but is, however, free to rotate relative to sleeve 12. The unit formed by sleeve 12 and ring 10 is then slid over body 2 of handpiece 1, until beads 22 engage in radial groove 24. Finally, tool shank 6 is passed through the through hole 48 delimited by ring 10 until shank 6 is rigidly coupled to drive shaft 8 via clamp 4. Ring 10 is thereby friction coupled to tool shank 6, such that when drive shaft 8 of handpiece 1 rotates, it simultaneously drives tool shank 6 and ring 10. Ring 10 thus rotates at the same speed as tool shank 6. It will be noted that the rigid coupling between drive shaft 8 of handpiece 1 and tool shank 6 does not form part of the invention and those skilled in the art are very familiar with the means used for such coupling. These means will not therefore be described here.

As already mentioned above, ring 10 is mounted on sleeve 12 which is itself removably mounted on body 2 of handpiece 1. For this purpose, on the rear end side of handpiece 1, sleeve 12 includes means for elastically fastening it to body 2 of handpiece 1 and, on the front end side of handpiece 1, means for mounting ring 10 so that said ring rotates freely. The means for elastically coupling sleeve 12 to body 2 of handpiece 1 are formed by the aforementioned arms 18, which, via their beads 22 engage in radial groove 24. The means for mounting ring 10 so that it rotates freely includes circular inner shoulder 50 provided in sleeve 12 on the front end side of handpiece 1.

Figure 6:
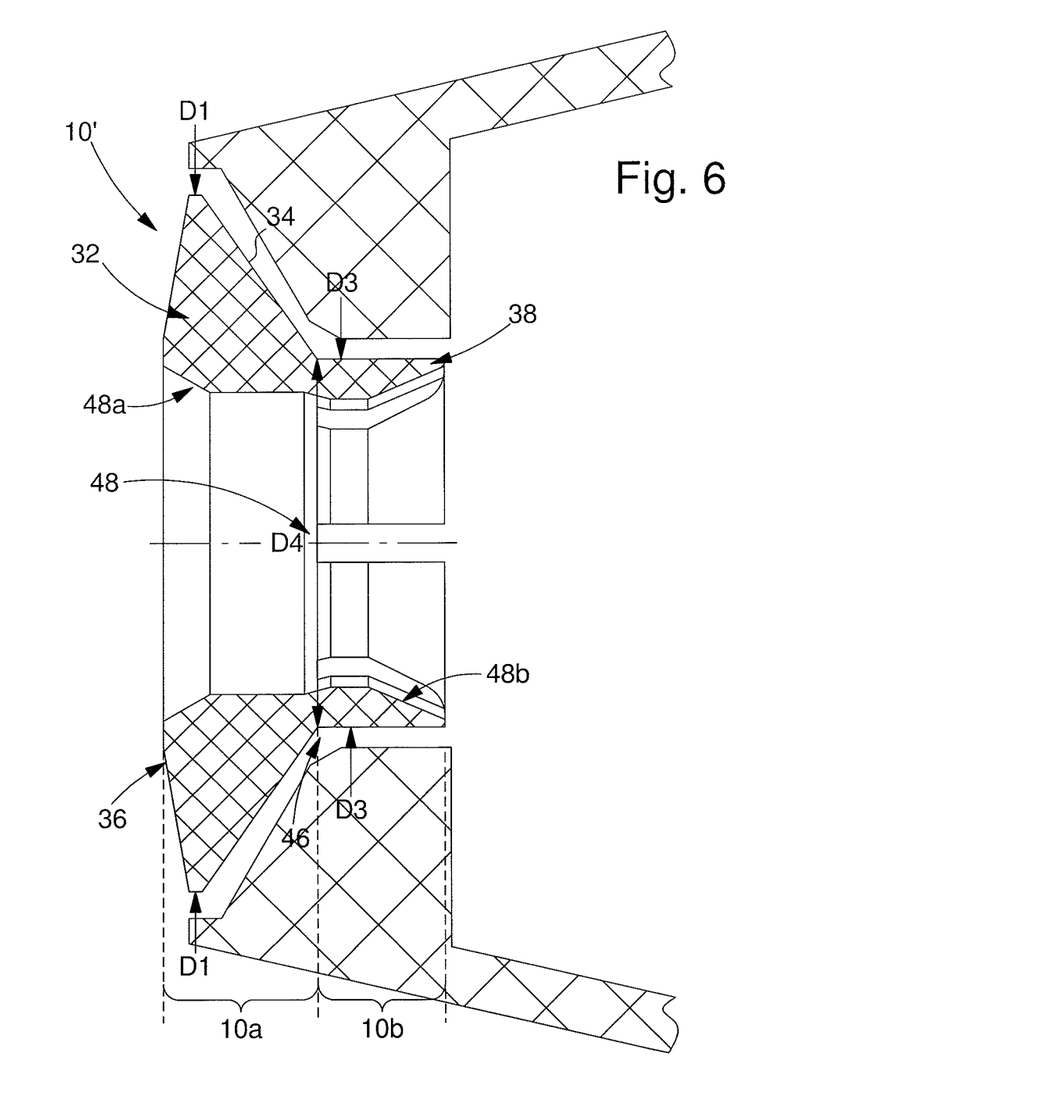
FIG. 6 is a similar view to that of FIG. 5 showing a ring intended to be secured by being driven onto the tool shank.

By way of variant, FIG. 6 shows a similar ring 10' to ring 10 described above and which differs only in that shoulders 40 have been omitted. This ring 10' is intended to be fixedly mounted by being driven onto tool shank 6. In this regard, it is sufficient to adjust the inner diameter of ring 10' relative to the outer diameter of tool shank 6 to allow said ring to be driven thereon.

The deflection device according to the invention operates as follows. As mentioned above, ring 10 is driven in rotation at the same speed as tool shank 6. An air flow is thus created in ejection chamber 11. Diameter D1 of the front part of flange 32 at outlet 35 of ejection chamber 11 is larger than the diameter D4 of the rear part of flange 32 at inlet 31 of ejection chamber 11. Consequently, when ring 10 rotates with tool shank 6, the circumferential speed of flange 32 is higher in the front part than in the back part thereof. The air flow velocity around the outer periphery of the front part of flange 32 is thus higher than the air flow speed around the outer periphery of the rear part of flange 32. Thus the air pressure around the front part of flange 32 is lower than the pressure at the rear part of flange 32. Thus, inside ejection chamber 11 of handpiece 1, between inlet 31 and outlet 35, a pressure gradient is created which decreases from the area of shoulders 40 towards the area of flange 32 located at the front end of handpiece 1. The effect of this pressure gradient creates an air flow which is ejected from handpiece 1 through outlet 35 of ejection chamber 11 and which expels the debris from the operating field through the front of the handpiece. Consequently, owing to the centrifugal deflection device according to the invention, the foreign matter present in the operating field does not penetrate the handpiece at all. The risk of damaging the handpiece mechanism is prevented and cleaning and sterilising operations are greatly simplified.

The materials used for making ring 10 and sleeve 12 can be machined or injected plastic, metal, ceramics or even a combination of these different materials. If sleeve 12 is made of plastic material, the plastic can be loaded with a heat sensitive pigment whose colour changes with temperature so as to make any heating of sleeve 12 visually apparent. The practitioner, who is alerted, will wait the time necessary for the sleeve to cool down and return to its original colour before inserting the instrument in the patient's mouth again. The risk of burning the patient's mouth is thus prevented. If sleeve 12 is made for example of metal or ceramics, it is possible to apply a layer of heat sensitive material onto sleeve 12 which will play the same part as the heat sensitive pigment embedded in the plastic material.

Figure 7:
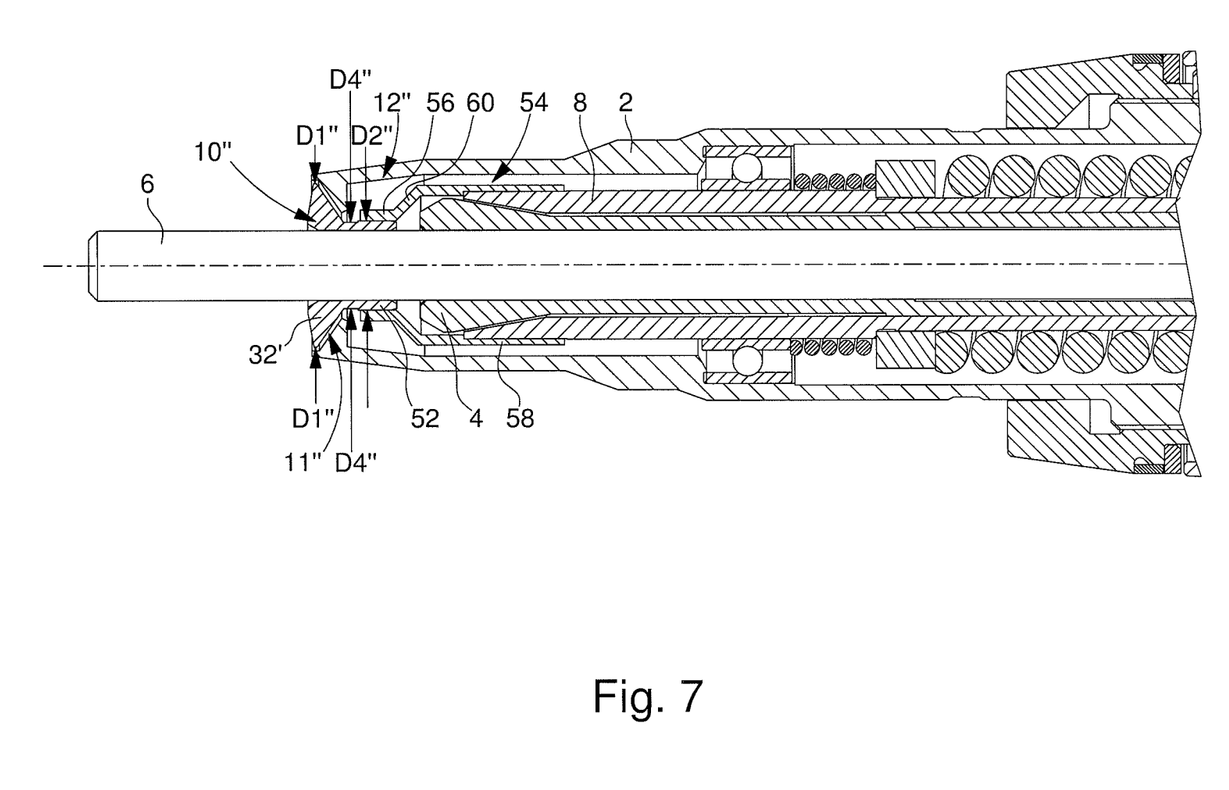
FIG. 7 shows a longitudinal cross-section of a handpiece fitted with a variant of the deflection device according to the invention.

FIG. 7 is a longitudinal cross-section of a handpiece fitted with another variant of the deflection device according to the invention. According to this embodiment, sleeve 12" is made in a single piece with body 2 of handpiece 1. Sleeve 12" covers a ring 10" slidably mounted on tool shank 6. This ring 10" includes, on the front end side of handpiece 1, a flange 32" of generally truncated shape whose diameter D1" decreases towards the rear end of handpiece 1. This flange 32" is extended towards the rear of handpiece 1 by a sleeve 52" whose external diameter D2" is smaller than the largest diameter D1" of flange 32". The opposite walls of ring 10" and sleeve 12" extend substantially parallel to each other and at a short distance relative to the difference between the largest diameter D1" and the smallest diameter D4" of conical ring 10" so as to delimit an annular chamber 11" with a substantially constant width. Ring 10" is coupled in rotation to drive shaft 8 of handpiece 1 by a coupling part 54 which includes cylindrical front 56 and back 58 portions connected to each other by an intermediate truncated portion 60. Coupling part 54 is engaged on drive shaft 8 via its rear cylindrical portion 58 and on sleeve 52 of ring 10" by the front cylindrical portion 56 thereof. Thus, the inner diameter of the rear cylindrical portion 58 of coupling part 54 is substantially equal to the external diameter of drive shaft 8 so as to allow coupling part 54 to be assembled on drive shaft 8, for example by being driven or welded thereon. The inner diameter of front cylindrical portion 56 of coupling part 54 is smaller than the outer diameter of sleeve 52 of ring 10" to allow ring 10" and drive shaft 8 to be rigidly coupled to each other. According to a variant, coupling part 54 can be made in a single piece with ring 10", the assembly then being driven or welded onto drive shaft 8 of handpiece 1.

Figure 8:
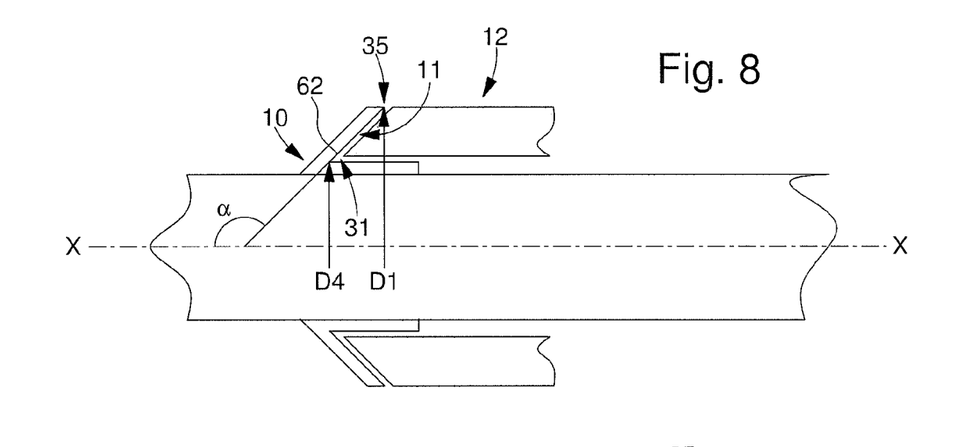
FIG. 8 is a schematic diagram of a ring driven onto the tool shank, said ring having an angle of taper which increases from the front end of the handpiece towards the rear end of the handpiece.
Figure 9:
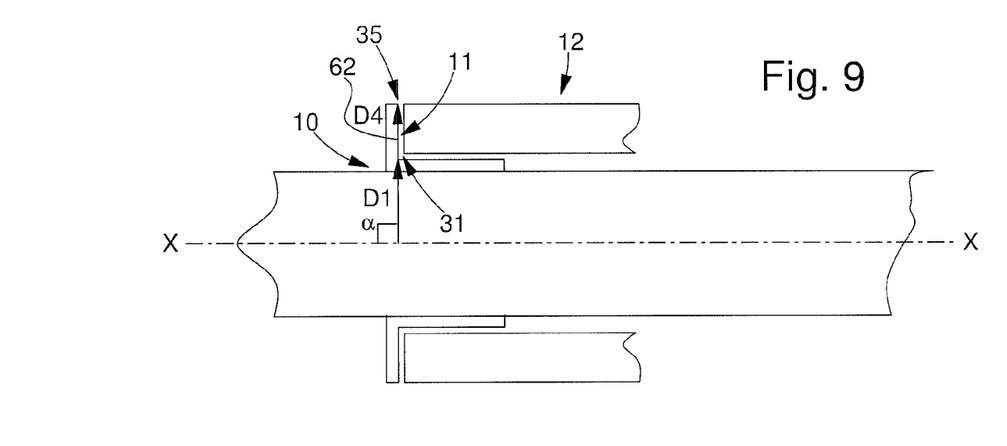
FIG. 9 is a schematic diagram of a ring driven onto a tool shank, said ring extending perpendicularly to the longitudinal axis of symmetry of the tool shank.

As can be seen upon examining FIG. 5, profile 62 of ejection chamber 11 forms an angle α of around 45° with axis of symmetry X-X of tool shank 6. In other words, the diameter of ejection chamber 11 decreases from the front end towards the back end of the handpiece. Other angle values may however be envisaged. Thus, as schematically shown in FIG. 8, the angle formed between profile 62 of ejection chamber 11 and the axis of symmetry X-X of tool shank 6 may be approximately 135°, without changing the operating principle of the centrifugal deflection device according to the invention. Indeed, although the diameter of profile 62 of ejection chamber 11 increases from the front end towards the back end of the handpiece, the first diameter D1 of ring 10 at outlet 35 of ejection chamber 11 is always larger than the second diameter D4 of ring 10 at inlet 31 of ejection chamber 11. Finally, in a last case illustrated in FIG. 9, it is even possible to envisage profile 62 of ejection chamber 11 being perpendicular to the axis of symmetry X-X of tool shank 6. Indeed, even in this case, the first diameter D1 of ring 10 is still located at the outlet point 35 of ejection chamber 11, whereas the second diameter D4 of ring 10 is located at the inlet point 31 of ejection chamber 11. Since the second diameter D4 is smaller than the first diameter D1, the air speed at inlet point 31 of ejection chamber 11 is lower than the air speed at the outlet point 35 of said ejection chamber 11. Consequently, the air pressure at inlet point 31 is higher than the air pressure at outlet point 35, so that a pressure gradient is created in ejection chamber 11 under the effect of which air will be expelled from the ejection chamber towards the exterior.

What is claimed is:

1. A centrifugal deflection device, which is fitted to a surgical or dental handpiece for preventing the penetration of foreign matter that results from an operation, said centrifugal deflection device including:
   a ring coupled in rotation via a shank of a tool to a drive shaft of the handpiece, the ring being covered by an outer sleeve fixed to a front end of a body of the handpiece, and which, with the ring, delimits an ejection chamber, said ejection chamber including an inlet that communicates with a rear area of the handpiece and an outlet that communicates with the external environment, the ring having a first diameter at the outlet of the ejection chamber, and a second diameter at the inlet of the ejection chamber, the first diameter of the ring being larger than the second diameter of the ring,
   wherein the sleeve is removably mounted on the body of the handpiece, the ring being free to rotate but axially locked by the sleeve, and
   wherein the ring is a revolution part including a conical section with a diameter which continuously decreases from the first diameter of the ring to the second diameter of the ring such that air pressure at the outlet of the ejection chamber is lower than air pressure at the inlet of the ejection chamber during rotation of the ring wherein the first diameter of the ring is smaller than an inner diameter of the sleeve at the outlet of the ejection chamber.

2. The device according to claim 1, wherein a profile of the ejection chamber and an axis of symmetry of the tool form a non-zero angle that extends on either side of a range centered around a value of 90°, which corresponds to a position in which the profile of the ejection chamber is perpendicular to the axis of symmetry of the tool.

3. The device according to claim 2, wherein opposite walls of the rotating ring and the fixed sleeve extend substantially parallel to each other.

4. The device according to claim 1, wherein the materials used to make the ring and the sleeve are machined or injected plastic, metal or a ceramic material or a combination of these different materials.

5. The device according to claim 4, wherein the sleeve is made of plastic material, wherein the plastic material is loaded with a heat sensitive pigment whose color changes with temperature so as to make any heating of the sleeve visually apparent.

6. The device according to claim 4, wherein, the sleeve is made of metal or ceramic material, wherein the metal or ceramic material is coated with a layer of heat sensitive material.

7. A centrifugal deflection device, which is fitted to a surgical or dental handpiece for preventing the penetration of foreign matter that results from an operation, said centrifugal deflection device including:
   a ring coupled in rotation via a shank of a tool to a drive shaft of the handpiece, the ring being covered by a sleeve fixed to a front end of a body of the handpiece, and which, with the ring, delimits an ejection chamber, said ejection chamber including an inlet that communicates with a rear area of the handpiece and an outlet that communicates with the external environment, the ring having a first diameter at the outlet of the ejection chamber, and a second diameter at the inlet of the ejection chamber, the first diameter of the ring being larger than the second diameter of the ring,
   wherein the sleeve is removably mounted on the body of the handpiece, the ring being free to rotate but axially locked relative to the sleeve,
   wherein a profile of the ejection chamber and an axis of symmetry of the tool form a non-zero angle that extends on either side of a range centered around a value of 90°, which corresponds to a position in which the profile of the ejection chamber is perpendicular to the axis of symmetry of the tool,
   wherein opposite walls of the rotating ring and the fixed sleeve extend substantially parallel to each other,
   wherein the ring is a revolution part including a conical section, the first diameter of which decreases from a front end towards a rear end of the handpiece, and
   wherein the conical section of the ring is extended towards the rear end of the handpiece by a rear section for axially locking the ring with respect to the sleeve, a largest diameter of the rear section being smaller than the largest diameter of the conical section of the ring.

8. The device according to claim 7, wherein the rear section of the ring is of substantially cylindrical shape.

9. The device according to claim 8, wherein the ring includes a flange centered on the tool shank, where a diameter of the flange decreases towards the rear end of the handpiece, said flange being extended by a plurality of arms extending tangentially around the tool shank and ending at a free end thereof in a plurality of shoulders, wherein a largest diameter of the flange being larger than a largest diameter of the shoulders.

10. The device according to claim 9, wherein the shoulders, with the flange, delimit a circular groove whose diameter is smaller than the largest diameter of the shoulders.

11. The device according to claim 10, wherein from the front end to the rear end of the handpiece, the shoulders have a cylindrical section extended by a truncated portion, whose diameter decreases towards the rear end of the handpiece.

12. The device according to claim 11, wherein an inner diameter of the ring is smaller than an external diameter of the tool shank.

13. The device according to claim 12, wherein on a rear end side of the handpiece, the sleeve includes means for elastically fastening said sleeve to the body of the handpiece and, on a front end side of the handpiece, means for mounting the ring so that said ring rotates freely.

14. The device according to claim 13, wherein, to fasten the sleeve to the body of the handpiece, said sleeve includes a plurality of regularly spaced arms which, on a face thereof facing the body of the handpiece, have beads which engage in an opposite radial groove provided on the body of the handpiece.

15. The device according to claim 14, wherein, on the front end side of the handpiece, the sleeve includes a circular inner shoulder which engages elastically in the circular groove.

* * * * *